(12) United States Patent
Chan et al.

(10) Patent No.: US 7,838,550 B2
(45) Date of Patent: *Nov. 23, 2010

(54) SELECTIVE N-SULFONYLATION OF 2-AMINO FLUORO- AND TRIFLUOROALKYL SUBSTITUTED ALCOHOLS

(75) Inventors: Anita Wai-Yin Chan, Fort Lee, NJ (US); Jianxin Ren, Nanuet, NY (US); Mousumi Ghosh, Elmwood Park, NJ (US); Panolil Raveendranath, Monroe, NY (US)

(73) Assignee: Wyeth LLC, Madison, NJ (US)

( * ) Notice: Subject to any disclaimer, the term of this patent is extended or adjusted under 35 U.S.C. 154(b) by 580 days.

This patent is subject to a terminal disclaimer.

(21) Appl. No.: 11/706,938

(22) Filed: Feb. 15, 2007

(65) Prior Publication Data

US 2007/0197800 A1  Aug. 23, 2007

Related U.S. Application Data

(60) Provisional application No. 60/774,300, filed on Feb. 17, 2006.

(51) Int. Cl.
 *C07D 333/32* (2006.01)
 *A61K 31/38* (2006.01)

(52) U.S. Cl. .......................... 514/445; 549/64

(58) Field of Classification Search ............... None
 See application file for complete search history.

(56) References Cited

U.S. PATENT DOCUMENTS

| | | | |
|---|---|---|---|
| 5,795,890 | A | 8/1998 | Nakae et al. |
| 5,962,231 | A | 10/1999 | Yue et al. |
| 6,362,178 | B1 | 3/2002 | Niewohner et al. |
| 6,476,029 | B1 | 11/2002 | Niewohner et al. |
| 6,610,734 | B2 | 8/2003 | Kreft et al. |
| 6,657,070 | B2 | 12/2003 | Resnick |
| 6,667,342 | B1 | 12/2003 | Clarke et al. |
| 6,683,081 | B2 | 1/2004 | Niewohner et al. |
| 6,800,764 | B2 | 10/2004 | Kreft et al. |
| 6,803,365 | B2 | 10/2004 | Niewohner et al. |
| 6,878,742 | B2 | 4/2005 | Kreft et al. |
| 7,166,622 | B2 | 1/2007 | Kreft et al. |
| 7,687,666 | B2 * | 3/2010 | Chan et al. ............ 564/468 |
| 2003/0013892 | A1 | 1/2003 | Resnick |
| 2004/0006050 | A1 | 1/2004 | Kreft et al. |
| 2004/0063737 | A1 | 4/2004 | Lucking et al. |
| 2004/0198778 | A1 | 10/2004 | Kreft et al. |
| 2005/0171180 | A1 | 8/2005 | Resnick et al. |
| 2007/0037778 | A1 | 2/2007 | Kreft et al. |

FOREIGN PATENT DOCUMENTS

| | | |
|---|---|---|
| EP | 769498 | 4/1997 |
| JP | 09241262 | 9/1997 |
| JP | 11343279 | 12/1999 |
| WO | WO-03-063797 | 8/2003 |
| WO | WO-03/076437 | 9/2003 |
| WO | WO-03/088908 | 10/2003 |
| WO | WO-03/103660 | 12/2003 |
| WO | WO-2004/078731 | 9/2004 |
| WO | WO-2004/092155 | 10/2004 |

OTHER PUBLICATIONS

Berry et al., "A Convenient Method for the Preparation of Enantiomerically Pure 2-Substituted N-Tosylaziridines", Synlett., 1:41-44 (Jan. 1992).
Bowman et al., "A Facile Method for the N-Alkylation of α-Amino Esters", Tet. 53(46):15787-15798 (Nov. 17, 1997).
Chataigner et al., "Discovery of a New Efficient Chiral Ligand for Copper-Catalyzed Enantioselective Michael Additions by High-Throughput Screening of a Parallel Library", Ang. Chem. Int. Ed., 39(5):916-918 (Mar. 3, 2000).
Cintrat et al., "Preparation of Chiral 2-Stannyloxazolidines and First Considerations on the Transacetalisation Reaction Mechanism", Eur. J. Org. Chem, 20:4251-4267 (Oct. 2004).
Egboh et al., "Synthesis and Characterization of Some Polyurethane Ionomers", Polymer, 23(8):1167-1171 (Jul. 1982).
Gandon et al., "Tris(trimethylsilyl)silane: An Unprecedented Enhancement in the Diastereoselectivity of Radical Cyclisations to Give 2,4-Disbstituted Piperidines", Org. & Biomolec. Chem. 2(16):2270-2271 (2004; Epub date Jul. 19, 2004).
Ghosh et al., "Chelation-controlled Ester-Derived Titanium Enolate Aldol reaction: Diastereoselective syn-aldols with mono- and Bidentate Aldehydes", Tet. Lett., 43(32):5621-5624 (Aug. 5, 2002).
Fuji et al., "Ring Opening of Optically Active CIS-Disubstituted Aziridino Alcohols: An Enantiodivergent Synthesis of Functionalized Amino Alcohol Derivatives", Heterocycles, 42(2):701-722 (1996).
Hedley et al., "Development of a [3+3] Cycloaddition Strategy Toward Functionalized Piperidines", J. Org. Chem., 68(11):4286-4292 (Jan. 3, 2003: Epub date Apr. 22, 2003).
Hudlicky et al., "JOC Additions and Corrections", J. Org. Chem, 68(2):674 (2003: Epub date Jan. 1, 2003).
Hudlicky et al., "Total Synthesis and Biological Evaluation of Amaryllidaceae Alkaloids: Narciclasine, ent-7-Deoxypancratistatin, Regioisomer of 7-Deoxypancratistatin, 10b-epi-Deoxypancratistatin, and Truncated Derivatives", J. Org. Chem., 67(25):8726-8743 (2002: Epub date Jul. 26, 2002).
Ibuka et al., "Aza-Payne Rearrangement of Activated 2-Aziridinemethanols and 2,3-Epoxy Amines Under Basic Conditions", J. Org. Chem., 60(7):2044-2058 (1995).
Ibuka et al., "Unprecedented Rearrangement Reaction of 2-Aziridinemethanols with "Lower Order" Lithium Methylcyanocuprate", Tet. Lett., 34(46):7421-7424 (Nov. 12, 1993).

(Continued)

*Primary Examiner*—Sun Jae Y Loewe
(74) *Attorney, Agent, or Firm*—Michael J. Herman; Howson & Howson LLP

(57) ABSTRACT

Processes for preparing sulfonamide trifluoroalkyl substituted alcohol compounds are provided. Desirably, the compounds are heterocyclic sulfonamide trifluoroalkyl substituted alcohol compounds or phenyl sulfonamide trifluoroalkyl substituted alcohol compounds.

16 Claims, No Drawings

OTHER PUBLICATIONS

Ibuka et al., "A Thermodynamic Preference of Chiral N-Methanesulfonyl and N-Arenesulfonyl 2,3-cis-3-Alkyl-2-Vinylaziridines over Their 2,3-Trans-Isomers: Useful Palladium(0)-Catalyzed Equilibration Reactions for the Synthesis of (E)-Alkene Dipeptide Isosteres", J. Org. Chem., 62(4):999-1015 (1997).

Moran et al., "A Concise Asymmetric Route to Nuphar Alkaloids. A Formal Synthesis of (-)-Deoxynupharidine", Org. Lett., 5(19):3427-3429 (Jun. 23, 2003: Epub date Aug. 28, 2003).

Ohno et al., "A 2,3-Cis-Selective Synthesis of Aziridines Bearing a Vinyl Group from Allyl Methyl Carbonates and Allyl Mesylates", J. Chem. Soc, Perkin Trans. 1, 22:3703-3716 (1998).

Ohno et al., "Stereodivergent Synthesis of Chiral 2-Alkenylaziridines: Palladium(0)-Catalyzed 2,3-cis-Selctive Aziridination and Base-Mediated 2,3-trans-Selective Aziridination", Chem. & Pharm. Bull., 52(1):111-119 (Jan. 2004).

Ohno et al., "Palladium(0)-Catalyzed Stereoselective Cyclization of Allenenes: Divergent Synthesis of Pyrrolidines and 3-Azabicyclo[3.1.0]Hexanes from Single Allenenes", J. Org. Chem., 69(13):4541-4544 (2004: Epub date May 28, 2004).

Otsuka et al., "Catalytic Asymmetric Reduction of Acetophenone Using Optically Active N-Sulfonyloxazaborolidine as a Catalyst", Memoirs of the Faculty of Science, Kyushu Univ., Series C: Chemistry 19(1):23-28 (1993).

Su et al., "Stereochemical Diversity Through Cyclodimerization: Synthesis of Polyketide-like Macrodiolides", Org. Lett., 5(12):2149-2152 (2003: Epub date May 15, 2003).

Tanner et al., "Studies of Regio- and Stereoselectivity in Some Nucleophilic Ring Opening Reactions of N-Tosyl-3-Phenyl-2-Aziridinemethanols and Derivatives", Tet. 51(30):8279-8288 (Jul. 24, 1995).

Tanner et al., "Regioselective Nucleophilic Ring Opening of 2,3-Aziridino Alcohols", Tet. 48(29):6069-6078 (1992).

Takahashi et al., "Synthesis and Absolute Configuration of Optically Pure 4-Isopropyl-N-Tosyl-1,3-Oxazolidines", Heterocycles 33(1):281-290 (1992).

Wanner et al., "A Dual Metathesis Route to Oligomeric Sulfonamides", Tet. Lett., 43(6):917-921 (Feb. 4, 2002).

Atsushi, "3-Oxa-2,7-diazabicyclo(3.3.0)octane Derivative", English abstract of Japanese Patent No. 09-241262 (Sep. 16, 1997).

Shionogi & CO LTD., "Sulfonamide Derivatives are TNF-α Inhibitors", English abstract of Japanese Patent No. 11-343279 (Dec. 14, 1999).

Chemical Diversity Research Institute, "Quinoline-Carboxylic Acids and the Derivatives Thereof, A Focused Library", English abstract of International Patent Publication No. WO-2004/078731.

Tanner et al., "Enanoselective Routes toward 1β-Methylcarbapenems from Chiral Aziridines", Tetrahedron, 48(29):6079-6086, (1992).

Otsuka et al., "Borane O-Adduct can be an intermediate in Chiral N-Sulfonyloxazaborolidine-Catalyzed Enantioselective Reduction of Ketones", SYNLETT, (May 1995).

Abiko et al., "New isoxazolidine-based chiral auxiliaries for asymmetric syntheses", Tetrahedron Letters, 38(18):3261-3264 (1997).

Reddy et al., "A practical protocol for chemoselective N-methylation of vicinal amino alcohols", Tetrahedron Letters, 41:949-951 (2000).

Altava et al., "A general route for the preparation of polymer-supported N-tosyl aminoalcohols and their use as chiral auxiliaries", Tetrahedron Letters, 42:1673-1675 (2001).

Brüggeman et al., "Stereoselective formation of quaternary carbon centres with chiral 3-sulfonyl-1,3-oxazolidines and titanium enolates", Tetrahedron, 58:321-340 (2002).

Bartels et al., "Asymmetric Ir[1]-Catalysed Allylic Alkylation of monosubstituted allylic acetates with phosphorus amidites as ligands", Eur. J. Org. Chem., 1097-1103 (2003).

Ohno et al., "Synthesis of Allenes from Allylic alcohol derivatives bearing a bromine atom using a palladium(0)/Diethylzinc system", J. Org. Chem., 67(4):1359-1367 (Feb. 22, 2002).

Aversa et al., "L-Cysteine, a Versatile Source of Sulfenic Acids. Synthesis of Enantiopure Alliin Analogues", J. Org. Chem., 70(6):1986-1992 (Mar. 18, 2005).

Dondoni et al., "Design and Use of an Oxazolidine Silyl Enol Ether as a New Homoalanine Carbanion Equivalent for the Synthesis of Carbon-Linked Isosteres of O-Glycosyl Serine and N-Glycosyl Asparagine", J. Org. Chem., 64(3):933-944 (Feb. 5, 1999).

Sham et al., "Renin Inhibitors. Design and Synthesis of a New Class of Conformationally Restricted Analogs of Angiotensinogen", J. Med. Chem., 31(2):284-295 (Feb. 1988).

* cited by examiner

SELECTIVE N-SULFONYLATION OF 2-AMINO FLUORO- AND TRIFLUOROALKYL SUBSTITUTED ALCOHOLS

CROSS-REFERENCE TO RELATED APPLICATIONS

This application claims the benefit of the priority of U.S. Provisional Patent Application No. 60/774,300, filed Feb. 17, 2006.

BACKGROUND OF THE INVENTION

This invention relates to inhibitors of beta amyloid production, which have utility in the treatment of Alzheimer's disease.

Alzheimer's Disease (AD) is the most common form of dementia (loss of memory) in the elderly. The main pathological lesions of AD found in the brain consist of extracellular deposits of beta amyloid protein in the form of plaques and angiopathy and intracellular neurofibrillary tangles of aggregated hyperphosphorylated tau protein. Recent evidence has revealed that elevated beta amyloid levels in the brain not only precede tau pathology but also correlate with cognitive decline. Further suggesting a causative role for beta amyloid in AD, recent studies have shown that aggregated beta amyloid is toxic to neurons in cell culture.

Heterocyclic- and phenyl-sulfonamide compounds, specifically fluoro- and trifluoroalkyl-containing heterocyclic sulfonamide compounds, have been shown to be useful for inhibiting β-amyloid production.

What is needed in the art are alternate processes for preparing sulfonamide compounds useful for inhibiting β-amyloid production.

SUMMARY OF THE INVENTION

In one aspect, processes for preparing sulfonamide trifluoroalkyl substituted alcohols are provided.

In another aspect, processes for preparing sulfonamide trifluoroalkyl substituted alcohols of the following structures are provided:

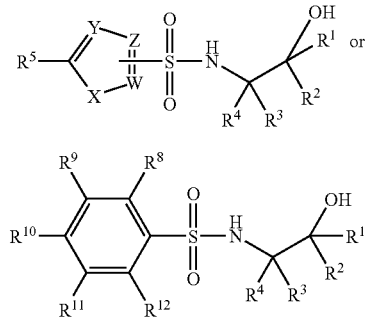

Formula I

Formula II

In a further aspect, processes for preparing sulfonamide trifluoroalkyl substituted alcohols of the following structure are provided:

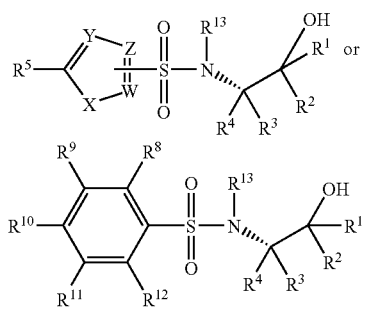

In yet another aspect, a process is provided for preparing 5-chloro-[N-(1S)-3,3,3-trifluoro-1-(hydroxymethyl)-2-(trifluoromethyl)propyl]thiophene-2-sulfonamide.

In still a further aspect, a process is provided for preparing 4-chloro-[N-(1S)-3,3,3-trifluoro-1-(hydroxymethyl)-2-(trifluoromethyl)propyl]benzenesulfonamide.

Other aspects and advantages of the invention will be readily apparent from the following detailed description of the invention.

DETAILED DESCRIPTION OF THE INVENTION

Processes are provided for preparing sulfonamide substituted compounds. Desirably, the processes are for preparing trifluoroalkyl-containing heterocyclic or phenyl sulfonamide compounds. A route to trifluoroalkyl-containing heterocyclic or phenyl sulfonamide compounds is therefore provided from the corresponding trifluoroalkyl aminoalcohol and sulfonyl chloride via only 1 step. This process also avoids the need for any protection and deprotection steps.

In one embodiment, the following trifluoroalkyl-containing heterocyclic or phenyl sulfonamide compounds are prepared.

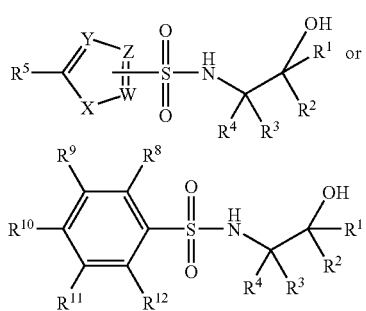

wherein, $R^1$ and $R^2$ are independently selected from among H, $C_1$ to $C_6$ alkyl, substituted $C_1$ to $C_6$ alkyl, $CF_3$, $C_2$ to $C_6$ alkenyl, substituted $C_2$ to $C_6$ alkenyl, $C_2$ to $C_6$ alkynyl, and substituted $C_2$ to $C_6$ alkynyl; $R^3$ is selected from among H, $C_1$ to $C_6$ alkyl and substituted $C_1$ to $C_6$ alkyl; $R^4$ is selected from among $(CF_3)_n$alkyl, $(CF_3)_n$(substituted alkyl), $(CF_3)_n$alkyl phenyl, $(CF_3)_n$alkyl(substituted phenyl), and $(F)_n$cycloalkyl; n is 1 to 3; $R^5$ is selected from among H, halogen, and $CF_3$; W, Y and Z are independently selected from among C, $CR^6$ and N, wherein at least one of W, Y or Z is C; X is selected from among O, S, $SO_2$, and $NR^7$; $R^6$ is selected from among H, halogen, $C_1$ to $C_6$ alkyl, and substituted $C_1$ to $C_6$ alkyl; $R^7$ is selected from among H, $C_1$ to $C_6$ alkyl, and $C_3$ to $C_8$ cycloalkyl; $R^8$, $R^9$, $R^{10}$, $R^{11}$, and $R^{12}$ are independently selected from among H, halogen, $C_1$ to $C_6$ alkoxy, substituted $C_1$ to $C_6$ alkoxy, $NO_2$, $C_1$ to $C_6$ alkyl, and substituted $C_1$ to $C_6$ alkyl; or $R^8$ and $R^9$; $R^9$ and $R^{10}$; $R^{11}$ and $R^{12}$; or $R^{10}$ and $R^{11}$ are fused to form (i) a carbon-based saturated ring containing 3 to 8 carbon atoms; (ii) a carbon-based unsaturated ring containing 3 to 8 carbon atoms; or (iii) a heterocyclic ring containing 1 to 3 heteroatoms selected from among O, N, and S in the backbone of the ring; wherein rings (i) to (iii) may be substituted by 1 to 3 substituents including $C_1$ to $C_6$ alkyl or substituted $C_1$ to $C_6$ alkyl; or a pharmaceutically acceptable salt, hydrate, or prodrug thereof.

In one embodiment, $R^1$-$R^3$ are H or $C_1$-$C_6$ alkyl. In one example, $R_1$-$R_3$ are H. In another example, $R^1$ and $R^2$ are $CH_3$ and $R^3$ is H. In a further example, $R^1$ is $CH_3$ and $R^2$ and $R^3$ are H.

In another embodiment, $R^4$ is $(CF_3)_n$alkyl or $(F)_n$cycloalkyl. In one example, $R^4$ is $(CF_3)_2CH$. In another example, $R^4$ is

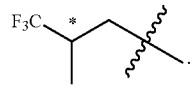

In a further example, $R^4$ is $(CH_2CF_3)_2CH$. In still another example, $R^4$ is $CF_3CH_2(CH_3)CH$. In yet another example, $R^4$ is $(F)_2$cycloalkyl.

In a further embodiment, $R^5$ is halogen.

In another embodiment, the following trifluoroalkyl-containing heterocyclic or phenyl sulfonamide compounds are provided, where $R^1$-$R^5$, $R^8$-$R^{12}$, W, X, Y, and Z are defined above.

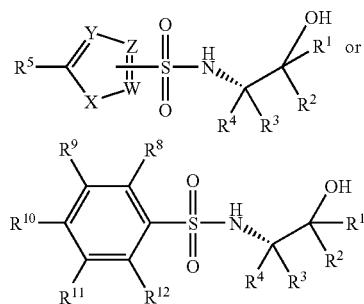

The point of attachment of the W-X-Y-Z-C heterocyclic ring to the $SO_2$ group is not a limitation. The ring may be attached to the $SO_2$ group through a carbon-atom or nitrogen-atom.

In one example, the compounds are thiophenesulfonamides, and more desirably 5-halo thiophene sulfonamides, and most desirably 5-halo thiophene sulfonamides with β-branches in the side chain of a primary alcohol.

In another example, the compounds are furansulfonamides. Thus, the compounds have a structure in which X is O. In one desirable embodiment, the furansulfonamides are characterized by β-branches in the side chain of a primary alcohol.

In a further example, the compounds are pyrazole sulfonamides. Thus, the compound has a structure in which X is $NR^7$, W is N and Z and Y are C or $CR^6$, with the proviso that at least one of Y or Z must be C.

In another example, the sulfonamide trifluoroalkyl substituted alcohol is 5-Chloro-N-[(1S)-3,3,3-trifluoro-1-(hydroxymethyl)-2-(trifluoromethyl)propyl]thiophene-2-sulfonamide or 4-Chloro-N-[(1S)-3,3,3-trifluoro-1-(hydroxymethyl)-2-(trifluoromethyl)propyl]benzenesulfonamide.

In yet another example, $R^1$ to $R^3$ are H, $R^4$ is $(CF_3)_2CH$, desirably of S-stereochemistry, $R^5$ is halogen, and W=C, X=S, Y=CH, Z=CH with the sulfonamide attached to C-2 of the thiophene ring.

In a further example, $R^1$ to $R^3$ are H, $R^5$ is halogen, W=C, X=S, Y=CH, Z=CH with the sulfonamide attached to C-2 of the thiophene ring and $R^4$ is of the structure:

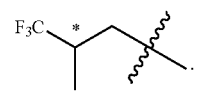

In another example, $R^1$ to $R^3$ are H, $R^4$ is $(CH_2CF_3)_2CH$, $R^5$ is halogen, and W=C, X=S, Y=CH, Z=CH with the sulfonamide attached to C-2 of the thiophene ring.

In a further example, $R^1$ and $R^2$ are $CH_3$, $R^3$ is H, $R^4$ is $CF_3CH_2(CH_3)CH$, $R^1$ is halogen, and W=C, X=S, Y=CH, Z=CH with the sulfonamide attached to C-2 of the thiophene ring.

In still another example, $R^1$ is $CH_3$, $R^2$ is H, $R^3$ is H, $R^4$ is $(CF_3)_2CH$, $R^5$ is halogen, and W=C, X=S, Y=CH, Z=CH with the sulfonamide attached to C-2 of the thiophene ring.

In yet a further example, $R^1$ to $R^3$ are H, $R^4$ is $(F)_2$cycloalkyl, $R^5$ is halogen, and W=C, X=S, Y=CH, Z=CH with the sulfonamide attached to C-2 of the thiophene ring.

The processes to form the sulfonamide trifluoroalkyl substituted alcohols thereby includes reacting a trifluoroalkyl substituted amino alcohol and a sulfonyl halide, in a base/solvent system. See, Scheme 1. In one embodiment, the process includes reacting a trifluoroalkyl substituted amino alcohol, a sulfonyl chloride, and a base/solvent system. The inventors have found that by using specific base/solvent systems, higher yields of the sulfonamide product are obtained. The base/solvent systems include 4-methyl morpholine/isopropyl acetate; Hünig's base/tetrahydrofuran; 4-methyl morpholine/acetonitrile; 4-methyl morpholine/propionitrile; and 4-methyl morpholine/toluene.

Scheme 1

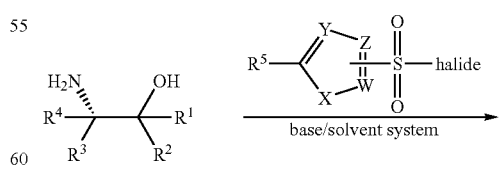

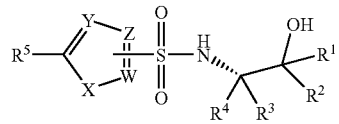

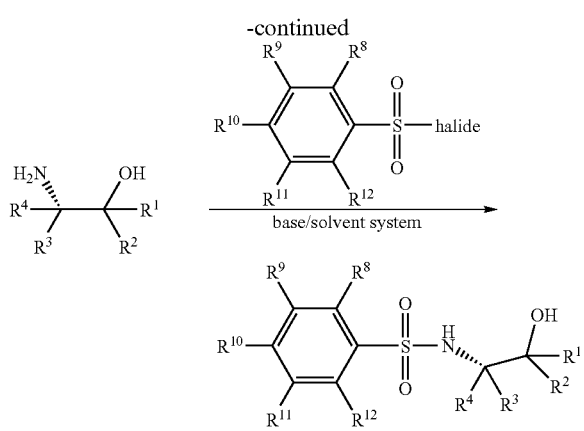

Desirably, the process is performed at a temperature of about −10 to about 80EC. More desirably, the process is performed at a temperature of about 0 to about 45EC.

The sulfonamide trifluoroalkyl substituted alcohols can thereby be isolated from the solvent/base system in high yields. In one embodiment, the sulfonamide trifluoroalkyl substituted alcohols are isolated by performing a solvent exchange. By doing so, highly pure sulfonamide trifluoroalkyl substituted alcohols are isolated. Desirably, the solvent utilized in the solvent/base system is exchanged for an anti-solvent. More desirably, the solvent utilized in the solvent/base system is slowly exchanged for an anti-solvent.

A variety of anti-solvents can be utilized to isolate highly pure sulfonamide trifluoroalkyl substituted alcohols and include heptane or an anti-solvent that has a polarity similar to heptane such as hexanes or cyclohexane. Desirably, the anti-solvent is heptane. One of skill in the art would readily be able to select a suitable anti-solvent for use in processes by using knowledge of skill in the art and the teachings provided herein.

In one embodiment, the trifluoroalkyl substituted amino alcohol is of the structure:

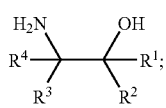

where $R^1$-$R^4$ are defined above. In another embodiment, the trifluoroalkyl substituted amino alcohol utilized is of the structure:

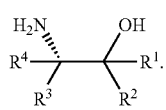

In one example, $R^4$ is $(CF_3)_n$alkyl such as $CF_3CH_2$, $CH(CH_3)CH_2CF_3$, $CH(CH_2CF_3)_2$, $CH(CF_3)CH_3$, or $CH(CF_3)_2$. In another example, $R^4$ is $(F)_n$cycloalkyl, desirably $(F)_2$cycloalkyl, more desirably $(F)_2$cyclohexane and bicyclo[3.1.0]hexane, and most desirably 4,4-difluoro-cyclohexane and 4,4-difluorobicyclo[3.1.0]-3-hexane. In a further example, the trifluoroalkyl substituted amino alcohol is a salt of (2S)-2-amino-4,4,4-trifluoro-3-(trifluoromethyl)butan-1-ol. In yet another embodiment, the trifluoroalkyl substituted amino alcohol is a (2S)-2-amino-4,4,4-trifluoro-3-(trifluoromethyl)butan-1-ol hydrochloride salt.

The sulfonyl chloride reacts with the trifluoroalkyl substituted alcohol. In one embodiment, the sulfonyl chloride is of the following structure, where $R^5$, W, X, Y, and Z are defined above. Desirably, $R^5$ is chloride.

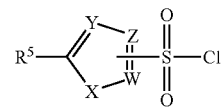

In one embodiment, the sulfonyl chloride is of the structure, where $R^5$ is defined above:

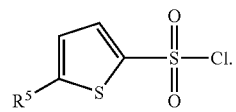

The sulfonyl chloride can also be of the structure, where $R^8$-$R^{12}$ are defined above:

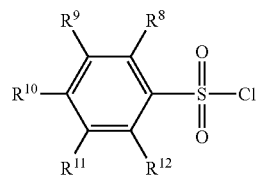

In another embodiment, the sulfonyl chloride is of the following structure, where $R^{11}$ is defined above and is at any position on the benzene ring including the ortho, meta, and para positions. Desirably, $R^{11}$ is halogen, nitro, $C_1$ to $C_6$ alkyl, or $C_1$ to $C_6$ alkoxy. More desirably, $R^{11}$ is chloride, nitro, methyl, or methoxy.

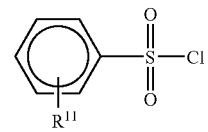

The compounds may contain one or more asymmetric carbon atoms and some of the compounds may contain one or more asymmetric (chiral) centers and may thus give rise to optical isomers and diastereomers. While shown without respect to stereochemistry, when the compounds contain one or more chiral centers, at least the chiral center of the β-amino alcohol is of S-stereochemistry. Desirably, the chiral centers include the carbon atom to which the N-atom, $R^3$, and $R^4$ are attached (the α-carbon atom), the carbon atom to which the OH, $R^1$, and $R^2$ are attached (the β carbon atom), or a combination thereof. More desirably, the α-carbon atom is chiral. Most desirably, the α-carbon atom is chiral and is of S-stereochemistry. Thus, the compounds include such optical isomers and diastereomers; as well as the racemic and resolved, enantiomerically pure stereoisomers; as well as other mixtures of the R and S stereoisomers, and pharmaceutically acceptable salts, hydrates, and prodrugs thereof.

The term "alkyl" is used herein to refer to both straight- and branched-chain saturated aliphatic hydrocarbon groups having one to ten carbon atoms (e.g., $C_1$, $C_2$, $C_3$, $C_4$, $C_5$, $C_6$, $C_7$, $C_8$, $C_9$, or $C_{10}$), such as one to eight carbon atoms (e.g., $C_1$, $C_2$, $C_3$, $C_4$, $C_5$, $C_6$, $C_7$, or $C_8$), one to six carbon atoms (e.g., $C_1$, $C_2$, $C_3$, $C_4$, $C_5$, or $C_6$), or one to four carbon atoms (e.g., $C_1$, $C_2$, $C_3$, or $C_4$). The term "lower alkyl" refers to straight- and branched-chain saturated aliphatic hydrocarbon groups having one to six carbon atoms (e.g., $C_1$, $C_2$, $C_3$, $C_4$, $C_5$, or $C_6$), desirably one to four carbon atoms (e.g., $C_1$, $C_2$, $C_3$, or $C_4$). The term "alkenyl" refers to both straight- and branched-chain alkyl groups with at least one carbon-carbon double bond and two to eight carbon atoms (e.g., $C_2$, $C_3$, $C_4$, $C_5$, $C_6$, $C_7$, or $C_8$), two to six carbon atoms (e.g., $C_2$, $C_3$, $C_4$, $C_5$, or $C_6$), or two to four carbon atoms (e.g., $C_2$, $C_3$, or $C_4$). The term "alkynyl" refers to both straight- and branched-chain alkyl groups with at least one carbon-carbon triple bond and two to eight carbon atoms (e.g., $C_2$, $C_3$, $C_4$, $C_5$, $C_6$, $C_7$, or $C_8$), two to six carbon atoms (e.g., $C_2$, $C_3$, $C_4$, $C_5$, or $C_6$), or two to four carbon atoms (e.g., $C_2$, $C_3$, or $C_4$).

The terms "substituted alkyl", "substituted alkenyl", and "substituted alkynyl" refer to alkyl, alkenyl, and alkynyl groups as just described having from one to three substituents including halogen, CN, OH, $NO_2$, amino, aryl, substituted aryl, heterocyclic, substituted heterocyclic, heteroaryl, substituted heteroaryl, alkoxy, substituted alkoxy, aryloxy, substituted aryloxy, alkylcarbonyl, alkylcarboxy, alkylamino, and arylthio. In one example, the substituent is selected from among halogen, CN, OH, $NO_2$, amino, aryl, heterocyclic, heteroaryl, alkoxy, aryloxy, alkylcarbonyl, alkylcarboxy, alkylamino, and arylthio. In another example, the substituent is selected from among halogen, CN, OH, $NO_2$, amino, aryl, heterocyclic, heteroaryl, and alkoxy. These substituents may be attached to any carbon of an alkyl, alkenyl, or alkynyl group provided that the attachment constitutes a stable chemical moiety.

The term "cycloalkyl" is used herein to describe a carbon-based saturated ring having more than 3 carbon-atoms and which forms a stable ring. The term cycloalkyl can include groups where two or more cycloalkyl groups have been fused to form a stable multicyclic ring. Desirably, cycloalkyl refers to a ring having about 4 to about 9 carbon atoms, and more desirably about 6 carbon atoms.

The term "substituted cycloalkyl" is used herein to refer to a cycloalkyl group as just described and having from one to five substituents including, without limitation, halogen, CN, OH, $NO_2$, amino, alkyl, substituted alkyl, alkenyl, substituted alkenyl, alkynyl, alkoxy, aryloxy, substituted alkyloxy, alkylcarbonyl, alkylcarboxy, alkylamino, substituted alkylamino, arylthio, heterocyclic, substituted heterocyclic, heteroaryl, substituted heteroaryl, aminoalkyl, and substituted aminoalkyl. In one example, the substituents are selected from among halogen, CN, OH, $NO_2$, amino, alkyl, alkenyl, alkynyl, alkoxy, aryloxy, alkylcarbonyl, alkylcarboxy, alkylamino, arylthio, heterocyclic, heteroaryl, and aminoalkyl. In another example, the substituents are selected from among halogen, CN, OH, $NO_2$, amino, alkyl, alkenyl, alkynyl, alkoxy, heterocyclic, and heteroaryl.

The term "aryl" is used herein to refer to a carbocyclic aromatic system, which may be a single ring, or multiple carbocyclic rings, desirably aromatic rings, fused or linked together such that at least one part of the fused or linked rings forms the conjugated aromatic system. The aryl groups include, but are not limited to, phenyl, naphthyl, biphenyl, anthryl, tetrahydronaphthyl, phenanthryl, and indane. Desirably, an aryl group has six to fourteen carbon atoms.

The term "substituted aryl" refers to aryl as just defined having one to four substituents including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, and arylthio. In one example, the substituent may be selected from among halogen, CN, OH, $NO_2$, amino, alkyl, cycloalkyl, alkenyl, alkynyl, alkoxy, aryloxy, alkylcarbonyl, alkylcarboxy, alkylamino, and arylthio. In another example, the substituent may be selected from among halogen, CN, OH, $NO_2$, amino, alkyl; cycloalkyl, alkenyl, alkynyl, and alkoxy.

The term "heterocycle" or "heterocyclic" as used herein can be used interchangeably to refer to a stable, saturated or partially unsaturated 3- to 9-membered monocyclic or multicyclic heterocyclic ring. The heterocyclic ring has in its backbone carbon atoms and one or more heteroatoms including nitrogen, oxygen, and sulfur atoms. In one embodiment, the heterocyclic ring contains 1 to about 4 heteroatoms in the backbone of the ring. When the heterocyclic ring contains nitrogen or sulfur atoms in the backbone of the ring, the nitrogen or sulfur atoms can be oxidized. The term "heterocycle" or "heterocyclic" also refers to multicyclic rings in which a heterocyclic ring is fused to an aryl ring of about 6 to about 14 carbon atoms. The heterocyclic ring can be attached to the aryl ring through a heteroatom or carbon atom provided the resultant heterocyclic ring structure is chemically stable. In one embodiment, the heterocyclic ring includes multicyclic systems having 1 to 5 rings.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Examples of heterocyclic groups include, without limitation, tetrahydrofuranyl, piperidinyl, 2-oxopiperidinyl, pyrrolidinyl, morpholinyl, thiamorpholinyl, thiamorpholinyl sulfoxide, pyranyl, pyronyl, dioxinyl, piperazinyl, dithiolyl, oxathiolyl, dioxazolyl, oxathiazolyl, oxazinyl, oxathiazinyl, benzopyranyl, benzoxazinyl and xanthenyl.

The term "heteroaryl" as used herein refers to a stable, aromatic 5- to 14-membered monocyclic or multicyclic heteroatom-containing ring. The heteroaryl ring has in its backbone carbon atoms and one or more heteroatoms including nitrogen, oxygen, and sulfur atoms. In one embodiment, the heteroaryl ring contains 1 to about 4 heteroatoms in the backbone of the ring. When the heteroaryl ring contains nitrogen or sulfur atoms in the backbone of the ring, the nitrogen or sulfur atoms can be oxidized. The term "heteroaryl" also refers to multicyclic rings in which a heteroaryl ring is fused to an aryl ring. The heteroaryl ring can be attached to the aryl ring through a heteroatom or carbon atom provided the resultant heterocyclic ring structure is chemically stable. In one embodiment, the heteroaryl ring includes multicyclic systems having 1 to 5 rings.

A variety of heteroaryl groups are known in the art and include, without limitation, oxygen-containing rings, nitrogen-containing rings, sulfur-containing rings, mixed heteroatom-containing rings, fused heteroatom containing rings, and combinations thereof. Examples of heteroaryl groups include, without limitation, furyl, pyrrolyl, pyrazolyl, imidazolyl, triazolyl, pyridyl, pyridazinyl, pyrimidinyl, pyrazinyl, triazinyl, azepinyl, thienyl, dithiolyl, oxathiolyl, oxazolyl, thiazolyl, oxadiazolyl, oxatriazolyl, oxepinyl, thiepinyl, diazepinyl, benzofuranyl, thionapthene, indolyl, benzazolyl, purindinyl, pyranopyrrolyl, isoindazolyl, indoxazinyl, benzoxazolyl, quinolinyl, isoquinolinyl, benzodiazonyl, napthylridinyl, benzothienyl, pyridopyridinyl, acridinyl, carbazolyl, and purinyl rings.

The term "substituted heterocycle" and "substituted heteroaryl" as used herein refers to a heterocycle or heteroaryl group having one or more substituents including halogen, CN, OH, $NO_2$, amino, alkyl, cycloalkyl, alkenyl, alkynyl, $C_1$ to $C_3$ perfluoroalkyl, $C_1$ to $C_3$ perfluoroalkoxy, alkoxy, aryloxy, alkyloxy including —O—($C_1$ to $C_{10}$ alkyl) or —O—($C_1$ to $C_{10}$ substituted alkyl), alkylcarbonyl including —CO—($C_1$ to $C_{10}$ alkyl) or —CO—($C_1$ to $C_{10}$ substituted alkyl), alkylcarboxy including —COO—($C_1$ to $C_{10}$ alkyl) or —COO—($C_1$ to $C_{10}$ substituted alkyl), —C($NH_2$)=N—OH, —$SO_2$—($C_1$ to $C_{10}$ alkyl), —$SO_2$—($C_1$ to $C_{10}$ substituted alkyl), —O—$CH_2$-aryl, alkylamino, arylthio, aryl, or heteroaryl, which groups may be optionally substituted. In one example, the substituents may be selected from among halogen, CN, OH, $NO_2$, amino, alkyl, cycloalkyl, alkenyl, alkynyl, $C_1$ to $C_3$ perfluoroalkyl, $C_1$ to $C_3$ perfluoroalkoxy, alkoxy, aryloxy, alkyloxy including —O—($C_1$ to $C_{10}$ alkyl) or —O—($C_1$ to $C_{10}$ substituted alkyl), alkylcarbonyl including —CO—($C_1$ to $C_{10}$ alkyl) or —CO—($C_1$ to $C_{10}$ substituted alkyl), alkylcarboxy including —COO—($C_1$ to $C_{10}$ alkyl) or —COO—($C_1$ to $C_{10}$ substituted alkyl), —C($NH_2$)=N—OH, —$SO_2$—($C_1$ to $C_{10}$ alkyl), —$SO_2$—($C_1$ to $C_{10}$ substituted alkyl), —O—$CH_2$-aryl, alkylamino, arylthio, aryl, or heteroaryl. In another example, the substituents may be selected from among halogen, CN, OH, $NO_2$, amino, alkyl, cycloalkyl, alkenyl, alkynyl, $C_1$ to $C_3$ perfluoroalkyl, $C_1$ to $C_3$ perfluoroalkoxy, alkoxy, aryl, or heteroaryl. A substituted heterocycle or heteroaryl group may have 1, 2, 3, or 4 substituents.

The term "alkoxy" is used herein to refer to the OR group, where R is alkyl or substituted alkyl. The term "lower alkoxy" refers alkoxy groups having one to six carbon atoms.

The term "aryloxy" is used herein to refer to the OR group, where R is aryl or substituted aryl.

The term "arylthio" is used herein to refer to the SR group, where R is aryl or substituted aryl.

The term "alkylcarbonyl" is used herein to refer to the RCO group, where R is alkyl or substituted alkyl.

The term "alkylcarboxy" is used herein to refer to the COOR group, where R is alkyl or substituted alkyl.

The term "aminoalkyl" refers to both secondary and tertiary amines wherein the alkyl or substituted alkyl groups, containing one to eight carbon atoms, which may be either same or different and the point of attachment is on the nitrogen atom.

The term "halogen" refers to $C_1$, Br, F, or I.

Pharmaceutically acceptable salts can be formed from organic and inorganic acids including, e.g., acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from inorganic bases, desirably alkali metal salts including, e.g., sodium, lithium, or potassium, and organic bases, such as ammonium salts, mono-, di-, and trimethylammonium, mono-, di- and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmono-ethanolammonium, and the like.

Physiologically acceptable alkali salts and alkaline earth metal salts can include, without limitation, sodium, potassium, calcium and magnesium salts in the form of esters, and carbamates.

These salts, as well as other compounds, can be in the form of esters, carbamates and other conventional "pro-drug" forms, which, when administered in such form, convert to the active moiety in vivo. In one embodiment, the prodrugs are esters. In another embodiment, the prodrugs are carbamates.

See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

In one embodiment, a process is provided for preparing 5-chloro-N-[(1S)-3,3,3-trifluoro-1-(hydroxymethyl)-2-(trifluoromethyl)propyl]thiophene-2-sulfonamide and includes reacting (2S)-2-amino-4,4,4-trifluoro-3-(trifluoromethyl)butan-1-ol, 5-chlorothiophene-2-sulfonyl chloride, and 4-methylmorpholine in isopropyl acetate. See, Scheme 2.

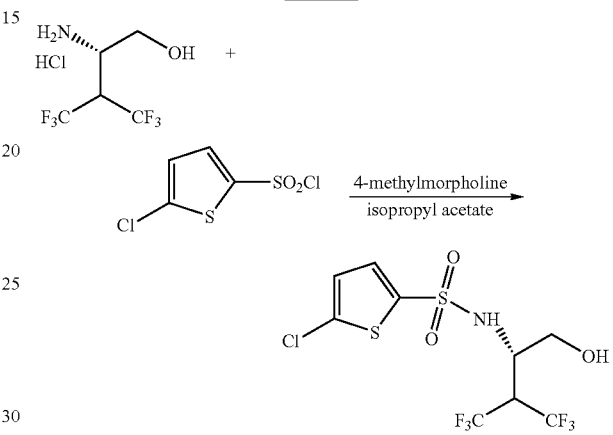

In another embodiment, a process is described for preparing 4-chloro-N-[(1S)-3,3,3-trifluoro-1-(hydroxymethyl)-2-(trifluoromethyl)propyl]benzenesulfonamide and includes reacting (2S)-2-amino-4,4,4-trifluoro-3-(trifluoromethyl)butan-1-ol, 4-chlorobenzene-2-sulfonyl chloride, and 4-methylmorpholine in isopropyl acetate. See, Scheme 3.

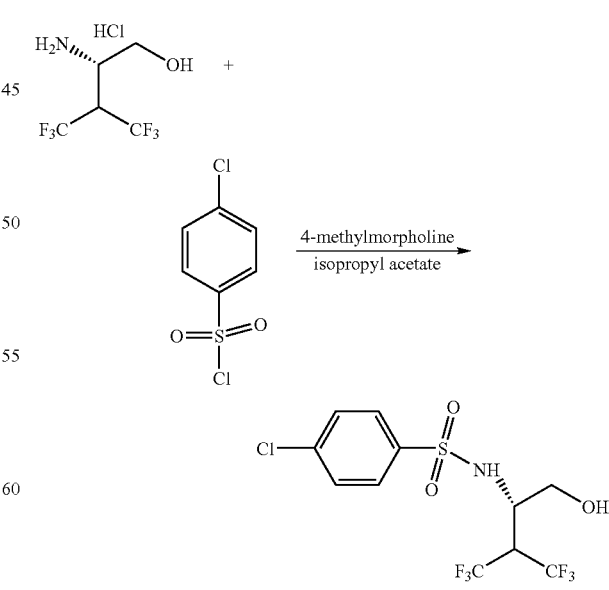

The following examples are illustrative only and are not intended to be a limitation on the present invention.

EXAMPLES

Example 1

Preparation of 5-Chloro-N-[(1S)-3,3,3-trifluoro-1-(hydroxymethyl)-2-(trifluoro-methyl)propyl]thiophene-2-sulfonamide To a suspension of (2S)-2-amino-4,4,4-tri-fluoro-3-(trifluoromethyl)butan-1-ol (2 g, 8.1 mmol) in isopropyl acetate (10 mL), 4-methyl morpholine (2.7 mL, 24.6 mmol) was added. The mixture was stirred at 20 to 25° C. for 5 to 10 minutes and then 5-chlorothiophene-2-sulfonyl chloride (2.0 g, 9.2 mmol) was added. The reaction mixture was stirred at 20 to 25° C. for 6 to 18 hours. Water (10 mL) was added to the reaction mixture and the solid dissolved. The two layers were separated, the organic layer was washed with 10% $NaHCO_3$ (10 mL) and 10% NaCl (10 mL), and heptane (10 mL) was added to the isopropyl acetate layer (about 10 mL). The mixture was reduced in volume by about half by distillation under atmospheric conditions. While the solution remained at 80 to 90° C., heptane (10 mL) was added over 5 to 10 minutes. A solid began to form during heptane addition. After addition, the mixture was cooled to 20 to 25° C., the solution was stirred for 1 to 2 hours, and then further cooled to 5 to 10° C. for 1 hour. The solid was collected by filtration, washed with heptane (5 mL), and oven-dried to give 2.15 g (67%) of an off-white solid. 98% area HPLC purity and >99% chiral purity by HPLC.

Example 2

Preparation of 4-Chloro-N-[(1S)-3,3,3-trifluoro-1-(hydroxymethyl)-2-(trifluoro-methyl)propyl]benzenesulfonamide To a suspension of (2S)-2-amino-4,4,4-tri-fluoro-3-(trifluoromethyl)butan-1-ol (5 g, 20.2 mmol) in isopropyl acetate (50 mL) was added 4-methyl morpholine (5 mL, 45.5 mmol). The mixture was stirred at 20 to 25° C. for 5 to 10 minutes and then 4-chlorobenzenesulfonyl chloride (4.5 g, 21.3 mmol) was added. The reaction mixture was stirred at 20 to 25° C. for 6 to 18 hours. Water (25 mL) was added to the reaction mixture and the solid dissolved. The two layers were separated, the organic layer was washed with 10% $NaHCO_3$ (25 mL) and 10% NaCl (25 mL), and heptane (50 mL) was added to the isopropyl acetate layer (about 50 mL). The mixture was reduced in volume by about half by distillation at atmospheric conditions. While the solution remained at 80 to 90° C., heptane (50 mL) was added over 5 to 10 minutes. A solid began to form during heptane addition. After addition, the mixture was cooled to 20 to 25° C., the solution was stirred for 1 to 2 hours, and then further cooled to 5 to 10° C. for 1 hours. The solid was collected by filtration, washed with heptane (15 mL), and oven-dried to give 6.44 g (83%) of an off-white solid. 98% area HPLC purity.

All publications cited in this specification are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A process for preparing a sulfonamide trifluoroalkyl substituted alcohol of the structure:

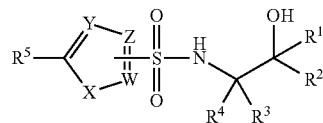

wherein:
R[1] and R[2] are independently selected from the group consisting of H and $C_1$ to $C_6$ alkyl;
R[3] is selected from the group consisting of H and $C_1$ to $C_6$ alkyl;
R[4] is $(CF_3)_n$alkyl;
n is 1 to 3;
R[5] is selected from the group consisting of H, halogen, and $CF_3$;
W, Y and Z are independently selected from the group consisting of C and CR[6], wherein at least one of W, Y or Z is C;
X is S;
R[6] is selected from the group consisting of H, halogen, $C_1$ to $C_6$ alkyl, and substituted $C_1$ to $C_6$ alkyl;
or a pharmaceutically acceptable salt or prodrug thereof;
said process comprising reacting a trifluoroalkyl substituted amino alcohol, a sulfonyl chloride, and a base/solvent system selected from the group consisting of (a) 4-methyl morpholine/isopropyl acetate, (b) Hünig's base/tetrahydrofuran, (c) 4-methyl morpholine/acetonitrile, (d) 4-methyl morpholine/propionitrile, and (e) 4-methyl morpholine/toluene.

2. The process according to claim 1, wherein said sulfonyl chloride is of the structure:

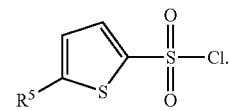

3. The process according to claim 2, wherein R[5] is chlorine.

4. The process according to claim 1, wherein said trifluoroalkyl substituted amino alcohol is of the structure:

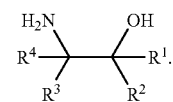

5. The process according to claim 1, wherein said trifluoroalkyl substituted amino alcohol is of the structure:

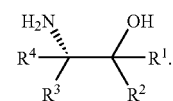

6. The process according to claim 1, wherein R[4] is $CH(CH_3)CF_3$.

7. The process according to claim 1, wherein said trifluoroalkyl substituted amino alcohol is (2S)-2-amino-4,4,4-trifluoro-3-(trifluoromethyl)butan-1-ol.

8. The process according to claim 7, wherein said sulfonamide trifluoroalkyl substituted alcohol is 5-Chloro-[N-[(1S)-3,3,3-trifluoro-1-(hydroxymethyl)-2-(trifluoromethyl)propyl]thiophene-2-sulfonamide.

9. The process according to claim 1, wherein said base/solvent system is isopropyl acetate and 4-methylmorpholine.

10. The process according to claim 1, wherein said base/solvent system is tetrahydrofuran and Hünig's base.

11. The process according to claim 1, wherein said base/solvent system is acetonitrile and 4-methyl morpholine.

12. The process according to claim 1, wherein said base/solvent system is propionitrile and 4-methyl morpholine.

13. The process according to claim 1, wherein said base/solvent system is toluene and 4-methyl morpholine.

14. The process according to claim 1, further comprising isolating said sulfonamide trifluoroalkyl substituted alcohol by performing a solvent exchange with heptane.

15. A process for preparing 5-chloro-[N-(1S)-3,3,3-trifluoro-1-(hydroxymethyl)-2-(trifluoromethyl)propyl]thiophene-2-sulfonamide, comprising reacting (2S)-2-amino-4,4,4-trifluoro-3-(trifluoromethyl)butan-1-ol, 5-chlorothiophene-2-sulfonyl chloride, and 4-methylmorpholine in isopropyl acetate.

16. The process according to claim 15, further comprising isolating said 5-chloro-[N-(1S)-3,3,3-trifluoro-1-(hydroxymethyl)-2-(trifluoromethyl)propyl]thiophene-2-sulfonamide by exchanging said isopropyl acetate with heptane.

* * * * *